United States Patent [19]

Hassall et al.

[11] Patent Number: 4,826,980
[45] Date of Patent: May 2, 1989

[54] PYRIDAZINE INTERMEDIATES

[75] Inventors: Cedric H. Hassall, Harpenden; Geoffrey Lawton, Hitchin; Sally Redshaw, Stevenage, all of England

[73] Assignee: Hoffmann-La Roche Inc., Nutley, N.J.

[21] Appl. No.: 217,805

[22] Filed: Jul. 12, 1988

Related U.S. Application Data

[62] Division of Ser. No. 48,172, May 11, 1987, Pat. No. 4,785,893, which is a division of Ser. No. 767,372, Aug. 12, 1985, Pat. No. 4,692,438.

[30] Foreign Application Priority Data

Aug. 24, 1984 [GB] United Kingdom ............... 8421493
May 29, 1985 [GB] United Kingdom ............... 8513541

[51] Int. Cl.[4] .................. C07D 237/24; C07D 237/18
[52] U.S. Cl. .................................................. 544/224
[58] Field of Search ........................................ 544/224

[56] References Cited

U.S. PATENT DOCUMENTS 4,692,438 9/1987 Hassall et al. ...................... 540/500

Primary Examiner—Robert T. Bond
Attorney, Agent, or Firm—Jon S. Saxe; Bernard S. Leon; William G. Isgro

[57] ABSTRACT

Compounds of the formula

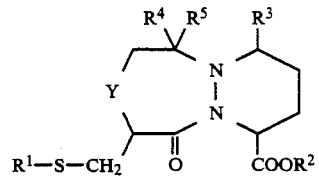

wherein $R^1$ is hydrogen, alkanoyl or aroyl; $R^2$ is hydrogen or alkyl; $R^3$ is hydrogen or aryl; $R^4$ and $R^5$ each are hydrogen or $R^4$ and $R^5$ taken together are oxo; and Y is $-CH_2-$, $-CH_2CH_2-$ or $-N(R^6)-$ in which $R^6$ is hydrogen, alkyl or aralkyl, as well as pharmaceutically acceptable salts thereof with bases when $R^2$ is hydrogen and pharmaceutically acceptable salts thereof with acids when Y is $-N(R^6)-$, which have antihypertensive activity and can be used as medicaments in the form of pharmaceutical preparations, are described.

The compounds of formula I contain at least one asymmetric carbon atom. Therefore, the invention comprises not only the optically uniform forms of these compounds, but also the various diastereoisomeric racemates and mixtures of different diastereoisomeric racemates.

1 Claim, No Drawings

PYRIDAZINE INTERMEDIATES

This is a division of application Ser. No. 48,172 filed May 11, 1987 which is a divisional of Ser. No. 764,372 filed Aug. 12, 1985.

BRIEF SUMMARY OF THE INVENTION

The invention relates to bicyclic compounds of the formula

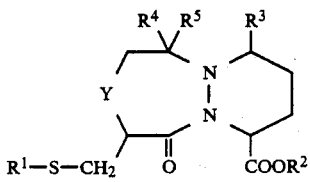

I wherein $R^1$ is hydrogen, alkanoyl or aroyl; $R^2$ is hydrogen or alkyl; $R^3$ is hydrogen or aryl; $R^4$ and $R^5$ each are hydrogen or $R^4$ and $R^5$ taken together are oxo; and Y is —$CH_2$—, —$CH_2CH_2$— or —$N(R^6)$— in which $R^6$ is hydrogen, alkyl or aralkyl, and their pharmaceutically acceptable salts with bases when $R^2$ is hydrogen and their pharmaceutically acceptable salts with acids when Y is —$N(R^6)$—.

The compounds of formula I contain at least one asymmetric carbon atom. Therefore, the invention comprises not only the optically uniform forms of these compounds, but also the various diastereoisomeric racemates and mixtures of different diastereoisomeric racemates.

DETAILED DESCRIPTION OF THE INVENTION

More particularly, the invention relates to bicyclic compounds of the formula

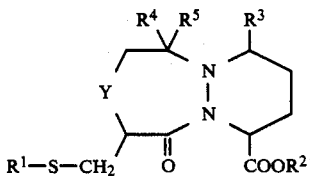

I wherein $R^1$ is hydrogen, alkanoyl or aroyl; $R^2$ is hydrogen or alkyl; $R^3$ is hydrogen or aryl; $R^4$ and $R^5$ each are hydrogen or $R^4$ and $R^5$ taken together are oxo; and Y is —$CH_2$—, —$CH_2CH_2$— or —$N(R^6)$— in which $R^6$ is hydrogen, alkyl or aralkyl, as well as pharmaceutically acceptable salts thereof with bases when $R^2$ is hydrogen and pharmaceutically acceptable salts thereof with acids when Y is —$N(R^6)$—.

The compounds of formula I contain at least one asymmetric carbon atom. Therefore, the invention embraces not only the optically uniform forms of these compounds, but also the various diastereoisomeric racemates and mixtures of different diastereoisomeric racemates. In the compounds of formula I, the configuration of the asymmetric carbon atoms bearing the $R^1$—S—$CH_2$— and $R^2OOC$— substituents is preferably (S).

As used herein, the term "alkyl" denotes a straight-chain or branched-chain alkyl group which contains from 1 to 8, preferably from 1 to 4, carbon atoms, for example, methyl, ethyl, propyl, isopropyl, butyl, tert-.butyl, pentyl, hexyl and the like. The term "aryl" denotes phenyl or phenyl carrying one or more substituents selected from halogen, alkyl, alkoxy, trifluoromethyl and the like, examples of aryl groups are phenyl, 4-chlorophenyl, p-tolyl, 4-methoxyphenyl and the like. The term "aralkyl" denotes an alkyl group in which one of the hydrogen atoms has been replaced by an aryl group, examples of aralkyl groups are benzyl, 2-phenylethyl, 3-phenylpropyl, 4-chloro-benzyl, 4-methoxybenzyl and the like. The term "alkanoyl" denotes an alkanoyl group derived from an alkanecarboxylic acid which contains up to 8 carbon atoms, preferably up to 4 carbon atoms, such as, acetic acid, propionic acid, butyric acid, valeric acid, pivalic acid and the like, and the term "aroyl" denotes an aroyl group derived from benzoic acid or a benzoic acid carrying one or more substituents selected from halogen, alkyl, alkoxy, trifluoromethyl and the like, such as, 4-chlorobenzoic acid, p-toluic acid, 4-methoxybenzoic acid and the like. The term "alkoxy" means an alkyl group linked via an oxygen atom, examples of alkoxy groups are methoxy, ethoxy, propoxy, isopropoxy, butoxy, tert-.butoxy, pentyloxy, hexyloxy and the like. The term "halogen" denotes fluorine, chlorine, bromine or iodine.

The compounds of formula I in which $R^2$ is hydrogen form pharmaceutically acceptable salts with bases. Examples of such salts are alkali metal salts, for example, sodium and potassium salts, alkaline earth metal salts, for example, calcium and magnesium salts, ammonium salts and salts with organic bases, such as, dicyclohexylamine and the like. The compounds of formula I in which Y is —$N(R^6)$— form pharmaceutically acceptable salts with acids, such as, mineral acids, for example, hydrochloric acid, hydrobromic acid, sulfuric acid, nitric acid and phosphoric acid, and organic acids, for example, acetic acid, maleic acid, fumaric acid, succinic acid, tartaric acid, citric acid, methanesulfonic acid, p-toluenesulfonic acid and the like.

A preferred class of compounds provided by the invention comprises those in which $R^1$ is hydrogen. $R^2$ preferably is hydrogen. With respect to $R^3$, this preferably is hydrogen. Y preferably is —$CH_2$—.

From the foregoing, it will be evident that particularly preferred compounds of formula I above are those in which $R^1$, $R^2$ and $R^3$ each are hydrogen and Y is —$CH_2$—.

Especially preferred compounds of formula I above are:
Octahydro-9-mercaptomethyl-6,10-dioxo-6H-pyridazo[1,2-a]-[1,2]diazepine-1-carboxylic acid; and
octahydro-9-mercaptomethyl-10-oxo-6H-pyridazo[1,2-a]-[1,2]-diazepine-1-carboxylic acid.

Examples of other interesting compounds of formula I are:
9-Acetylthiomethyl-octahydro-6,10-dioxo-6H-pyridazo-[1,2-a][1,2]diazepine-1-carboxylic acid,
9-acetylthiomethyl-octahydro-10-oxo-6H-pyridazo[1,2-a]-[1,2]diazepine-1-carboxylic acid,
tert.butyl 9-acetylthiomethyl-octahydro-6,10-dioxo-6H-pyridazo[1,2-a][1,2]diazepine-1-carboxylate and
tert.butyl 9-acetylthiomethyl-octahydro-10-oxo-6H-pyridazo-[1,2-a][1,2]diazepine-1-carboxylate.

Further examples of other interesting compounds of formula I above are:
Decahydro-10-mercaptomethyl-6,11-dioxo-6H-pyridazo-[1,2-a][1,2]diazocine-1-carboxylic acid, tert.butyl 10-acetylthiomethyl-decahydro-6,11-dioxo-6H-pyridazo[1,2-a][1,2]diazocine-1-carboxylate, 9-acetylthiomethyl-8-benzyl-octahydro-6,10-dioxo-6H-pyridazo[1,2-a][1,2,5]triazepine-1-carboxylic acid, 8-benzyl-octahydro-9-mercaptomethyl-6,10-6H-pyridazo-[1,2-a][1,2,5]triazepine-1-carboxylic acid, 9-acetylthiomethyl-8-methyl-octahydro-6,10-dioxo-6H-pyridazo[1,2-a][1,2,5]triazepine-1-carboxylic acid, octahydro-9-mercaptomethyl-8-methyl-6,10-dioxo-6H-pyridazo[1,2-a][1,2,5]triazepine-1-carboxylic acid, tert.butyl 9-acetylthiomethyl-8-benzyl-octahydro-6,10-dioxo-6H-pyridazo[1,2-a][1,2,5]triazepine-1-carboxylate, tert.butyl 9-acetylthiomethyl-8-methyl-octahydro-6,10-dioxo-6H-pyridazo[1,2-a][1,2,5]triazepine-1-carboxylate and methyl 9-acetylthiomethyl-octahydro-6,10-dioxo-6H-pyridazo[1,2-a][1,2]diazepine-1-carboxylate.

According to the process provided by the invention, the compounds of formula I and their pharmaceutically acceptable salts can be prepared as follows:

(a) for the preparation of a compound of formula I in which $R^4$ and $R^5$ together are oxo, reacting a compound of the formula

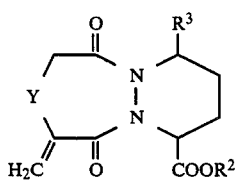

wherein $R^2$, $R^3$ and Y are as previously described, with a compound of the formula

wherein $R^1$ is as previously described, or (b) for the preparation of a compound of formula I in which $R^1$ is alkanoyl or aroyl, $R^2$ is alkyl and Y is $-CH_2-$, $-CH_2CH_2-$ or $-N(R^6)-$ in which $R^6$ is alkyl or aralkyl, reacting a compound of the formula

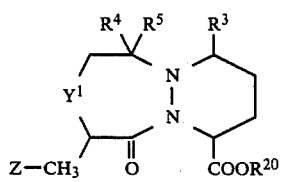

wherein $R^3$, $R^4$ and $R^5$ are as previously described, $R^{20}$ represents alkyl, $Y^1$ is $-CH_2-$, $-CH_2CH_2-$ or $-N(R^{60})-$ in which $R^{60}$ is alkyl or aralkyl, and Z is a leaving group, with an alkali metal salt of a compound of the formula

wherein $R^{10}$ is alkanoyl or aroyl, or (c) for the preparation of a compound of formula I in which $R^1$ is alkanoyl or aroyl, $R^2$ is alkyl, $R^4$ and $R^5$ taken together are oxo and Y is $-CH_2-$ or $-CH_2CH_2-$, cyclizing a compound of the formula

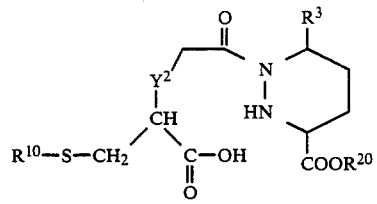

wherein $R^3$, $R^{10}$ and $R^{20}$ are as previously described and $Y^2$ is $-CH_2$ or $-CH_2CH_2-$, or (d) for the preparation of a compound of formula I in which $R^1$ is alkanoyl or aroyl, $R^2$ is alkyl, $R^4$ and $R^5$ taken together are oxo and Y is $-CH_2-$ or $-CH_2CH_2-$, cyclizing a compound of the formula

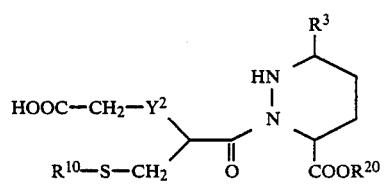

wherein $R^3$, $R^{10}$, $R^{20}$ and $Y^2$ are as previously described, or (e) for the preparation of a compound of formula I in which $R^1$ is alkanoyl or aroyl, $R^2$ is alkyl, $R^4$ and $R^5$ taken together are oxo and Y is $-NH-$, cyclizing a compound of the formula

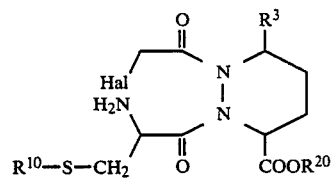

wherein $R^3$, $R^{10}$ and $R^{20}$ are as previously described and Hal is halogen, or (f) for the preparation of a compound of formula I in which $R^1$ is alkanoyl or aroyl, $R^2$ is alkyl and $R^4$ and $R^5$ each are hydrogen, reducing a compound of formula I in which $R^1$ is alkanoyl or aroyl, $R^2$ is alkyl and $R^4$ and $R^5$ taken together are oxo, or (g) for the preparation of a compound of formula I in which $R^1$ is alkanoyl or aroyl and Y is $-N(R^6)-$ in which $R^6$ is alkyl or aralkyl, reacting a compound of formula I in which $R^1$ is alkanoyl or aroyl and Y is $-NH-$ with a compound of the formula

wherein $R^{60}$ and Z are as previously described, or (h) for the preparation of a compound of formula I in which $R^1$ is hydrogen, treating a compound of formula I in which $R^1$ is alkanoyl or aroyl with a base, or (i) for the preparation of a compound of formula I in which $R^2$ is hydrogen, treating a compound of formula I in which $R^2$ is alkyl with an acid or a base, or (j) for the preparation of a compound of formula I in which $R^1$ is alkanoyl or aroyl and Y is $-CH_2-$, $-CH_2CH_2-$ or $-N(R^6)-$ in which $R^6$ is alkyl or aralkyl, appropriately alkanoylating or aroylating a corresponding compound of formula I in which $R^1$ is hydrogen, or (k) if desired, separating a mixture of diastereoisomeric racemates obtained into the diastereoisomeric racemates or optically pure diastereoisomers, and/or (l) if desired, resolving a racemate obtained into the optical antipodes, that is, enantiomers, and (m) if desired, converting a compound of formula I obtained in which $R^2$ is hydogen into a pharmaceutically acceptable salt with a base or converting a compound of formula I obtained in which Y is —$N(R^6)$— into a pharmaceutically acceptable salt with an acid.

The reaction of a compound of formula II with a compound of formula III in accordance with embodiment (a) of the process can be carried out in a known manner. The reaction can be carried out in the presence of absence of an inert organic solvent. When an inert organic solvent is used, this can be, for example, an aliphatic or aromatic hydrocarbon, for example, n-hexane, benzene, toluene and the like; a halogenated hydrocarbon, for example, dichloromethane, chloroform, 1,1,1-trichloroethane and the like;, an aliphatic or cyclic ether, for example, diethyl ether, glycol dimethyl ether, tetrahydrofuran, dioxane and the like; an amide, for example, dimethylformamide; an aliphatic ketone, for example, acetone, methyl ethyl ketone and the like; or the like. The preferred solvent is a halogenated hydrocarbon, particularly dichloromethane. The reaction temperature is not critical and can be in the range of from about room temperature to the reflux temperature of the reaction mixture. In a preferred aspect, the reaction is carried out at about room temperature.

The leaving group denoted by Z in compounds of formula IV used as starting materials in embodiment (b) of the process can be, for example, a halogen atom, such as, a chlorine or bromine atom, an alkylsulfonate group, such as, the methanesulfonate group or an arylsulfonate group, such as, the p-toluenesulfonate group.

The reaction of a compound of formula IV with an alkali metal salt of a compound of formula V in accordance with embodiment (b) of the process is conveniently carried out in the presence of an inert organic solvent. The alkali metal salt can be, for example, the sodium salt or, preferably, the potassium salt, and the reaction can be advantageously carried out in the presence of a catalytic amount of an alkali metal iodide, for example, sodium iodide, potassium iodide and the like. Suitable inert organic solvents are aliphatic ketones, for example, acetone, methyl ethyl ketone and the like; halogenated hydrocarbons, for example, dichloromethane, chloroform, 1,1,1-trichloroethane and the like; aliphatic esters, for example, ethyl acetate, butyl acetate and the like; amides, for example, dimethylformamide and the like; or the like. The reaction temperature is not critical. The reaction can be carried out, for example, at a temperature in the range of from about 10° C. to the reflux temperature of the reaction mixture. In a preferred procedure, the reaction is carried out at the reflux temperature of the reaction mixture.

The cyclization of a compound of formula VI in accordance with embodiment (c) of the process can be carried out in a known manner. In a preferred procedure, the cyclization is carried out by converting a compound of formula VI by treatment in a known manner with an appropriate halogenating agent, such as, a phosphorus pentahalide, for example, phosphorus pentachloride and the like, or a thionyl halide, for example, thionyl chloride into the corresponding acid halide, for example, acid chloride, which cyclizes spontaneously to the desired compound of formula I.

The cyclization of a compound of formula VII in accordance with embodiment (d) of the process can be carried out in a known manner. In a preferred procedure, the cyclization is carried out by converting a compound of formula VII by treatment in a known manner with an appropriate halogenating agent, such as, a phosphorus pentahalide, for example, phosphorus pentachloride and the like, or a thionyl halide, for example, thionyl chloride and the like, into the corresponding acid halide, for example, acid chloride, which cyclizes spontaneously to the desired compound of formula I.

The cyclization of a compound of formula VIII in accordance with embodiment (e) of the process can be carried out readily, for example, in the presence of a base, such as, an aqueous alkali metal carbonate or bicarbonate, for example, sodium bicarbonate and the like, and in the presence of an inert organic solvent, such as, an aliphatic or aromatic hydrocarbon, for example, n-hexane, benzene, toluene and the like; a halogenated hydrocarbon, for example, dichloromethane, chloroform, 1,1,1-trichloroethane and the like; an aliphatic or cyclic ether, for example, diethyl ether, glycol dimethyl ether, tetrahydrofuran, dioxane and the like; an amide, for example, dimethylformamide; an aliphatic ketone, for example, acetone, methyl ethyl ketone and the like; or the like. Although this cyclization is preferably carried out at about room temperature, it can also be carried out at an elevated temperature if desired, for example at a temperature up to the reflux temperature of the reaction mixture.

The reduction of a compound of formula I in which $R^1$ is alkanoyl or aroyl, $R^2$ is alkyl and $R^4$ and $R^5$ taken together are oxo, in accordance with embodiment (f) of the process, is conveniently carried out using a borane, expediently a complex of borane, such as, a borane/tetrahydrofuran, borane/dimethyl sulfide, borane/N,N-diethylaniline or like complex. This reduction with a borane is suitably carried out in an inert organic solvent and at a low temperature; for example, using a borane/tetrahydrofuran complex in tetrahydrofuran at about 0° C. to about 20° C.

The reaction of a compound of formula I in which $R^1$ is alkanoyl or aroyl and Y is —NH— with a compound of formula IX in accordance with embodiment (g) of the process can be carried out in a known manner. Suitably, the reaction is carried out in the presence of an inert organic solvent, such as, for example, a halogenated hydrocarbon, for example, dichloromethane, chloroform and the like; an amide, for example, dimethylformamide and the like; a nitrile, for example, acetonitrile and the like; or the like. If desired, the reaction can be carried out in the presence of an organic base, such as, a trialkylamine, for example, triethylamine, diethylisopropylamine and the like; pyridine; N,N-dimethylaniline; or the like. The reaction can be carried out at about room temperature or at an elevated temperature, for example, at the reflux temperature of the reaction mixture.

A compound of formula I in which $R^1$ is alkanoyl or aroyl is converted into a compound of formula I in which $R^1$ is hydrogen in accordance with embodiment (h) of the process by treatment with a base. This treatment can be carried out in a known manner. Suitable bases are alkali metal hydroxides, for example, sodium hydroxide and potassium hydroxide, as well as ammonium hydroxide. The treatment can be carried out at a temperature in the range of from about room temperature to the boiling point of the reaction mixture, advantageously at about room temperature.

The conversion of a compound of formula I in which $R^2$ is alkyl into a compound of formula I in which $R^2$ is hydrogen in accordance with embodiment (i) of the process is also carried out in a known manner by treatment with a base or, where the alkyl group is tert.butyl, by treatment with acid. This treatment can be carried out in a known manner. Suitable bases are alkali metal hydroxides, for example, sodium hydroxide and potassium hydroxide, as well as ammonium hydroxide. The treatment can be carried out at a temperature in the range of from about room temperature to the boiling point of the reaction mixture, advantageously at about room temperature. Anhydrous trifluoroacetic acid is an especially suitable acid for this purpose, with the treatment in this case being expediently carried out at about room temperature.

Known methods can be used for the alkanoylation or aroylation of a compound of formula I in which $R^1$ is hydrogen in accordance with embodiment (j) of the process. For example, the alkanoylation can be carried out by reacting the compound of formula I with a reactive derivative of an appropriate acid, for example, the acid chloride, in the presence of a base and in an inert organic solvent. Suitable bases are, for example, organic bases, such as, trialkylamines, for example, triethylamine and the like; pyridine; N,N-dimethylaniline; or the like, and suitable inert organic solvents are, for example, halogenated hydrocarbons, for example, dichloromethane, chloroform and the like; amides, for example, dimethylformamide and the like; or the like. The temperature at which this reaction is carried out is not critical and can vary in the range of from about room temperature to the reflux temperature of the reaction mixture.

The separation of diastereoisomeric mixtures into the diastereoisomeric racemates or optically pure diastereoisomers in accordance with embodiment (k) of the present process can be carried out according to known methods; for example, by chromatography, for example, on silica gel, using a suitable solvent system, for example, ethyl acetate/n-hexane.

The resolution of a racemate into the optical antipodes in accordance with embodiment (l) of the present process can be carried out according to known methods, for example, by treatment with an appropriate optically active acid or an appropriate optically active base, as the case may require, separating the optically active salts obtained, for example, by fractional crystallization, and, where required, liberating the optically uniform compounds from these salts by conventional methods.

The conversion of a compound of formula I in which $R^2$ is hydrogen into a pharmaceutically acceptable salt with a base and the conversion of a compound of formula I in which Y is $-N(R^6)-$ into a pharmaceutically acceptable salt with an acid in accordance with embodiment (m) of the process can be carried out by treatment with an appropriate base or acid in a conventional manner.

The compounds of formula II used as starting materials in embodiment (a) of the process also form part of the present invention.

The compounds of formula II can be prepared, for example, by cleaving the benzyloxycarbonyl group from a compound of the formula

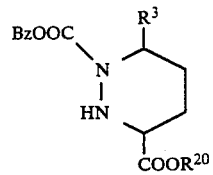

X wherein $R^3$ and $R^{20}$ are as previously described and Bz is benzyl, reacting the resulting compound of the formula

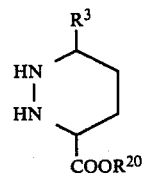

XI wherein $R^3$ and $R^{20}$ are as previously described, with an anhydride of the formula

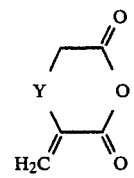

XII wherein Y is as previously described, cyclizing the resulting compound of the formula

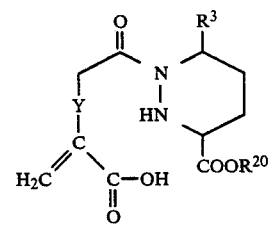

XIII wherein $R^3$, $R^{20}$ and Y are previously described, and, if desired, treating the resulting compound of formula II in which $R^2$ is alkyl with an acid or a base to give a corresponding compound of formula II in which $R^2$ is hydrogen and, also if desired, esterifying this compound to give a corresponding compound of formula II in which $R^2$ is alkyl.

The cleavage of the benzyloxycarbonyl group from a compound of formula X can be carried out according to known procedures, for example, using hydrogen in the presence of a catalyst, such as, a noble-metal catalyst, for example, palladium-on-carbon, and in the presence of an inert solvent, for example, an alkanol, such as, methanol and the like.

The resulting compound of formula XI is then reacted with an anhydride of formula XII to give a compound of formula XIII. This reaction is expediently carried out in an inert organic solvent, such as, a halogenated hydrocarbon or, preferably, an aliphatic or cyclic ether, for example, dioxane, at a temperature in the range of from about room temperature to the reflux temperature of the reaction mixture, preferably at room temperature.

The cyclization of a compound of formula XIII can be carried out in a known manner. In a preferred procedure, the cyclization is carried out by converting a compound of formula XIII by treatment in a known manner with an appropriate halogenating agent, such as, a phosphorus pentahalide, for example, phosphorus pentachloride and the like, or a thionyl halide, for example, thionyl chloride and the like, into the corresponding acid halide, for example, acid chloride, which cyclizes spontaneously to give a compound of formula II in which $R^2$ is alkyl.

A thus-obtained compound of formula II in which $R^2$ is alkyl, can be converted, if desired, into a compound of formula II in which $R^2$ is hydrogen by treatment with an acid or a base. This treatment can be carried out in a known manner. Suitable bases are alkali metal hydroxides, for example, sodium hydroxide and potassium hydroxide, as well as ammonium hydroxide. The treatment can be carried out at a temperature in the range of from about room temperature to the boiling point of the reaction mixture, advantageously at about room temperature.

The esterification of a compound of formula II in which $R^2$ is hydrogen can be carried out in a known manner, for example, by treatment with a suitable diazoalkane, such as, diazomethane.

An alternative procedure for the preparation of compounds of formula XIII above in which $R^{20}$ is tert.butyl and Y is —$CH_2$— or —$CH_2CH_2$— comprises reacting a compound of formula XI above in which $R^{20}$ is tert.butyl with a 1-($C_{1-3}$-alkyl) hydrogen 2-methylene-pentanedioate or -hexanedioate and treating the reaction product with a base.

The reaction of a compound of formula XI in which $R^{20}$ is tert.butyl with a 1-($C_{1-3}$-alkyl) hydrogen 2-methylene-pentanedioate or -hexanedioate can be carried out in a known manner. Suitably, the aforementioned half ester is converted into a reactive derivative, such as, an activated ester which is then reacted with the compound of formula XI, conveniently in an inert organic solvent, for example, an ether, such as, tetrahydrofuran and the like, and at a temperature in the range of from about 0° C. to room temperature.

The treatment of the reaction product with a base to give a compound of formula XIII in which $R^{20}$ is tert.butyl and Y is —$CH_2$— or —$CH_2CH_2$— can be carried out in a manner analogous to that described above in connection with the conversion of a compound of formula II in which $R^2$ is alkyl into a compound of formula II in which $R^2$ is hydrogen by treatment with a base.

The compounds of formula IV used as starting materials in embodiment (b) of the process also form part of the present invention.

The compounds of formula IV in which Y is —$CH_2$— or —$CH_2CH_2$— can be prepared, for example, by reacting a compound of formula X above with a compound of the formula

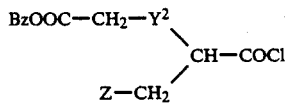

wherein $Y^2$, Z and Bz are as previously described, removing the benzyl and benzyloxycarbonyl groups from the resulting compound of the formula

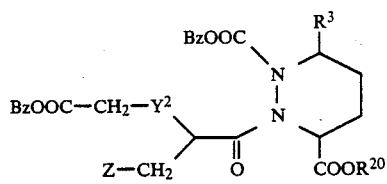

wherein $R^3$, $R^{20}$, $Y^2$, Z and Bz are as previously described, and cyclizing the resulting acid of the formula

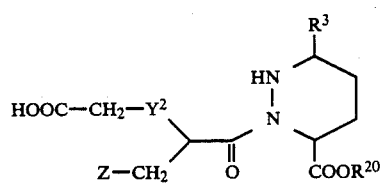

wherein $R^3$, $R^{20}$, $Y^2$ and Z are as previously described, and, if desired, reducing the resulting compound of formula IV in which $R^4$ and $R^5$ taken together are oxo and $Y^1$ is —$CH_2$ or —$CH_2CH_2$— to a corresponding compound of formula IV in which $R^4$ and $R^5$ each is hydrogen.

The reaction of a compound of formula X with a compound of formula XIV can be carried out in a conventional manner, for example, in an inert organic solvent, for example, a halogenated hydrocarbon, such as, dichloromethane, and in the presence of a base, for example, an alkali metal carbonate, such as, sodium carbonate, or an alkali metal bicarbonate, such as, sodium bicarbonate, suitably at about room temperature.

The removal of the benzyl and benzyloxycarbonyl groups from a compound of formula XV can be carried out according to generally known methods, for example, using hydrogen in the presence of a catalyst, such as, a noble-metal catalyst, for example, palladium-on-carbon, or, when $R^{20}$ is other than tert.butyl, using hydrogen bromide in glacial acetic acid.

The cyclization of an acid of formula XVI can be carried out in a known manner. In a preferred procedure, the cyclization is carried out by converting a compound of formula XVI by treatment in a known manner with an appropriate halogenating agent, such as, a phosphorus pentahalide, for example, phosphorus pentachloride and the like, or a thionyl halide, for example, thionyl chloride and the like, into the corresponding acid halide, for example, acid chloride, which cyclizes spontaneously to give a compound of formula IV in which $R^4$ and $R^5$ taken together are oxo and $Y^1$ is —$CH_2$— or —$CH_2CH_2$—.

The reduction of a compound of formula IV in which $R^4$ and $R^5$ taken together are oxo and $Y^1$ is —$Ch_2$— or —$CH_2CH_2$— is conveniently carried out using a borane, expediently a complex of borane, such as, a borane/tetrahydrofuran, borane/dimethyl sulfide, borane/N,N-diethylaniline or like complex. This reduction with a borane is suitably carried out in an inert organic solvent and at a low temperature; for example, using a borane/tetrahydrofuran complex in tetrahydrofuran at about 0° C. to about 20° C.

The compounds of formula IV in which $Y^1$ is —$N(R^{60})$— can be prepared, for example, by reacting a compound of formula XI above with a haloacetyl halide, reacting the resulting compound of the formula

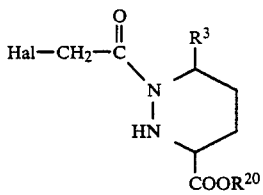   XVII wherein $R^3$, $R^{20}$ and Hal are as previously described, with a compound of the formula

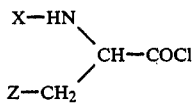   XVIII wherein Z is as previously described and X is an amino protecting group, cleaving the amino protecting group denoted by X in the resulting compound of the formula

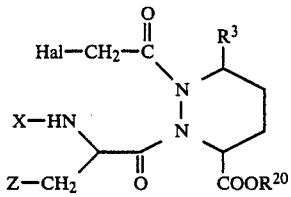   XIX wherein $R^3$, $R^{20}$, X, Z and Hal are as previously described, cyclizing the resulting compound of the formula

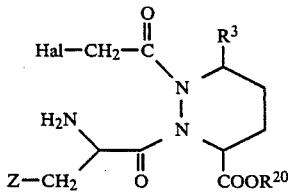   XX wherein $R^3$, $R^{20}$, Z and Hal are as previously described, reacting the resulting compound of the formula

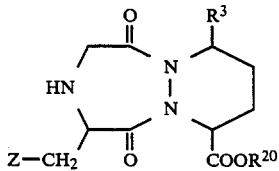   XXI wherein $R^3$, $R^{20}$ and Z are as previously described, with a compound of formula IX and, if desired, reducing the resulting compound of formula IV in which $R^4$ and $R^5$ taken together are oxo and $Y^1$ is —$N(R^{60})$— to a corresponding compound of formula IV in which $R^4$ and $R^5$ each is hydrogen.

The reaction of a compound of formula XI with a haloacetyl halide, such as, chloroacetyl chloride, bromoacetyl bromide, bromoacetyl chloride and the like, can be carried out in a known manner, for example, in an inert organic solvent, such as, a halogenated hydrocarbon, for example, dichloromethane and the like, and in the presence of a base, such as, an alkali metal carbonate or bicarbonate, for example, sodium bicarbonate and the like. Suitably, the reaction is carried out at a temperature from about 0° C. to about room temperature.

The amino protecting group denoted by X in formula XVIII can be any conventional amino protecting group. Preferably, X is an amino protecting group which is removable by treatment with a base, such as, the trifluoroacetyl group.

The reaction of a compound of formula XVII with a compound of formula XVIII can be carried out in a known manner. For example, the reaction can be carried out in an inert organic solvent, such as, a halogenated hydrocarbon, for example, dichloromethane and the like, and in the presence of a base, such as, an alkali metal carbonate or bicarbonate, for example, sodium bicarbonate and the like. The reaction is conveniently carried out at a temperature from about 0° C. to about room temperature.

The amino protecting group denoted by X in a compound of formula XIX is then cleaved in a known manner depending on the nature of the protecting group present to give a compound of formula XX.

The cyclization of a compound of formula XX can be carried out readily, for example, in the presence of a base, such as, an aqueous alkali metal carbonate or bicarbonate, for example, sodium bicarbonate and the like, and in the presence of an inert organic solvent, such as, an aliphatic or aromatic hydrocarbon, for example, n-hexane, benzene, toluene and the like; a halogenated hydrocarbon, for example, dichloromethane, chloroform, 1,1,1-trichloroethane and the like; an aliphatic or cyclic ether, for example, diethyl ether, glycol dimethyl ether, tetrahydrofuran, dioxane and the like; an amide, for example, dimethylformamide and the like; an aliphatic ketone, for example, acetone, methyl ethyl ketone and the like; or the like. Although this cyclization is preferably carried out at about room temperature, it can also be carried out at an elevated temperature, if desired, for example at a temperature up to the reflux temperature of the reaction mixture.

The aforementioned cleavage of the amino protecting group denoted by X and the cyclization can also be carried out in reverse order, if desired. For example, a compound of formula XIX can be cyclized by treatment with an alkali metal hydride, such as, sodium hydride in an inert organic solvent, such as, an amide, for example, dimethylformamide and the like, at about room temperature and the protecting group denoted by X can then be cleaved in a known manner.

The reaction of a compound of formula XXI with a compound of formula IX can be carried out in a known manner. Suitably, the reaction is carried out in the presence of an inert organic solvent, such as, for example, a halogenated hydrocarbon, for example, dichloromethane, chloroform and the like, an amide, for example, dimethylformamide and the like, a nitrile, for example, acetonitrile and the like, or the like. If desired, the reaction can be carried out in the presence of an organic base, such as, a trialkylamine, for example, triethylamine, diethylisopropylamine and the like, pyridine; N,N-dimethylaniline; or the like. The reaction can be carried out at about room temperature or at an elevated temperature, for example, at the reflux temperature of the reaction mixture.

The reduction of a compound of formula IV in which R⁴ and R⁵ taken together are oxo and Y¹ is —N(R⁶⁰)— is conveniently carried out using a borane, expediently a complex of borane, such as, a borane/tetrahydrofuran, borane/dimethyl sulfide, borane/N,N-diethylaniline or like complex. This reduction with a borane is suitably carried out in an inert organic solvent and at a low temperature, for example, using a borane/tetrahydrofuran complex in tetrahydrofuran at about 0° C. to about 20° C.

According to a variant of the procedure described above for the preparation of the compounds of formula IV in which Y¹ is —N(R⁶⁰)—, there is used in place of a compound of formula XVIII a corresponding compound in which Z is a protected hydroxy group, for example, benzyloxy. The protected hydroxy group is retained during the subsequent steps of the process until the cyclization has been effected, whereupon it is converted into a hydroxy group in a known manner. For example, when the protected hydroxy group is benzyloxy, this can be converted into hydroxy by catalytic hydrogenation in the presence of a noble-metal catalyst, such as, palladium. The resulting compound, corresponding to formula XXI but with Z being hydroxy, is then reacted with a compound of formula IX as described above and the product is converted into a compound of formula IV in which R⁴ and R⁵ taken together are oxo and Y¹ is —N(R⁶⁰)— in a known manner; for example, by reaction with an alkanesulfonyl halide, such as, methanesulfonyl chloride. Finally, if desired, the compound of formula IV obtained can be reduced as described above to give a corresponding compound in which R⁴ and R⁵ each is hydrogen.

The compounds of formula VI used as starting materials in embodiment (c) of the process also form part of the present invention.

The compounds of formula VI can be prepared, for example, by reacting a compound of formula XIII above in which Y is —CH₂— or —CH₂CH₂— with a compound of formula V above.

The reaction of a compound of formula XIII in which Y is —CH₂— or —CH₂CH₂— with a compound of formula V can be carried out in a known manner. The reaction can be carried out in the presence or absence of an inert organic solvent. When an inert organic solvent is used, this can be, for example, an aliphatic or aromatic hydrocarbon, for example, n-hexane, benzene, toluene and the like; a halogenated hydrocarbon, for example, dichloromethane, chloroform, 1,1,1-trichloroethane and the like; an aliphatic or cyclic ether, for example, diethyl ether, glycol dimethyl ether, tetrahydrofuran, dioxane and the like; an amide, for example, dimethylformamide; an aliphatic ketone, for example, acetone, methyl ethyl ketone and the like; or the like. The preferred solvent is a halogenated hydrocarbon, particularly dichloromethane. The reaction temperature is not critical and can be in the range of from about room temperature to the reflux temperature of the reaction mixture. In a preferred aspect, the reaction is preferably carried out at about room temperature.

The compounds of formula VII used as starting materials in embodiment (d) of the process also form part of the present invention.

The compounds of formula VII can be prepared, for example, by reacting a compound of formula X above with a compound of the formula

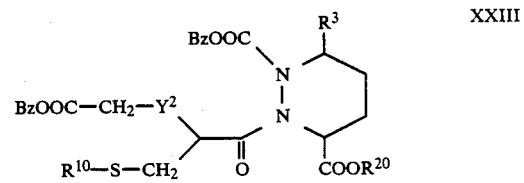

wherein R¹⁰, Y² and Bz are as previously described, and removing the benzyl and benzyloxycarbonyl groups from the resulting compound of the formula

wherein R³, R¹⁰, R²⁰, Y² and Bz are as previously described.

The reaction of a compound of formula X with a compound of formula XXII can be carried out in a conventional manner; for example, in an inert organic solvent, for example, a halogenated hydrocarbon, such as, dichloromethane, and in the presence of a base, for example, an alkali metal carbonate, such as, sodium carbonate, or an alkali metal bicarbonate, such as, sodium bicarbonate, suitably at about room temperature.

The removal of the benzyl and benyloxycarbonyl groups from a compound of formula XXIII can be carried out according to generally known methods; for example, using hydrogen in the presence of a catalyst, such as, a noble-metal catalyst, for example, palladium-on-carbon or, when R²⁰ is other than tert.butyl, using hydrogen bromide in glacial acetic acid.

The compounds of formula VIII used as starting materials in embodiment (e) of the process also form part of the present invention.

The compounds of formula VIII can be prepared, for example, by reacting a compound of formula XVII above with a compound of the formula

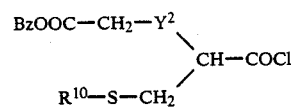

wherein R¹⁰ and X are as previously described, and cleaving the protecting group denoted by X in the resulting compound of the formula

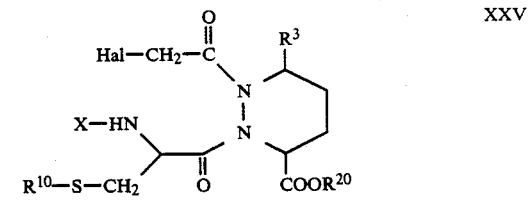

wherein R³, R¹⁰, R²⁰, X and Hal are as previously described.

The reaction of a compound of formula XVII with a compound of formula XXIV can be carried out in a known manner. For example, the reaction can be carried out in an inert organic solvent, such as, a halogenated hydrocarbon, for example, dichloromethane and the like, and in the presence of a base, such as, an alkali metal carbonate or bicarbonate, for example, sodium bicarbonate and the like. This reaction is suitably carried out at a temperature from about 0° C. to about room temperature.

The cleavage of the protecting group denoted by X in a compound of formula XXV is carried out in a manner known depending on the nature of the protecting group present.

The compounds of formulas III, V and IX used as starting materials in embodiments (a), (b) and (g) of the process are known compounds.

The compounds of formulas X, XII, XIV, XVIII, XXII and XXIV used in the preparation of the starting materials as described above are known compounds or analogues of known compounds which can be obtained in a similar manner to the known compounds.

The compounds of formula I and their aforementioned pharmaceutically acceptable salts are useful as antihypertensive agents. They inhibit angiotensin converting enzyme (ACE) which brings about the conversion of angiotensin I into angiotensin II and are therefore useful in reducing or alleviating angiotensin-related hypertension.

The activity of the compounds of formula I and the aforementioned salts in inhibiting angiotensin converting anzyme in vitro can be determined by the following test.

The method used in based on the method of Cushman and Cheung (Biochem. Pharmacol., 20. 1637–1648) incorporating the modifications introduced by Hayakari et al (Anal. Biochem., 84. 361-369). The substrate, which is hippuryl-histidyl-leucine, 2 mM, is incubated with angiotensin converting enzyme in the presence or absence of various concentrations of test substance in potassium phosphate buffer (pH 8.3; 100 mM) containing sodium chloride (300 mM) for 24 minutes at 37° C. (total value 500 μl). If the test substance is an ester, it is appropriate to cleave it by means of hog liver esterase before carrying out the test. The reaction is terminated by the addition of 3 ml of potassium phosphate buffer (pH 8.3; 200 mM) at 0° C. 2,4,6-Trichloro-s-triazine (3%) in 1.5 ml of dioxane and the mixture is agitated until the yellow chromophore has developed fully. The samples are then centrifuged to remove any precipitate which has formed. The yellow chromophore formed by the reaction of the 2,4,6-trichloro-s-triazine with free hippuric acid is measured spectrophoto metrically at 382 nm. The $IC_{50}$ values are defined as the concentration of test substance which reduces by 50% the cleavage of hippuryl-histidyl-leucine by angiotensin converting enzyme under the aforementioned conditions.

The results obtained in the foregoing test using representative compounds of formula I as the test substance are compiled in the following Table:

TABLE

| Compound | $IC_{50}$ (nM) |
| --- | --- |
| A | 4.0 |
| B | 2.6 |
| C | 19 |
| D | 51 |

TABLE-continued

Compound A = Octahydro-9(S)—mercaptomethyl-6,10-dioxo-6H—pyridazo[1,2-a][1,2]diazepine-1(S)—carboxylic acid.
Compound B = Octahydro-9(S)—mercaptomethyl-10-oxo-6H—pyridazo-[1,2-a][1,2]diazepine-1(S)—carboxylic acid.
Compound C = Decahydro-10(R,S)—mercaptomethyl-6,11-dioxo-6H—pyridazo[1,2-a][1,2]diazocine-1(S)—carboxylic acid.
Compound D = Octahydro-9-mercaptomethyl-8-methyl-6,10-dioxo-6H—pyridazo[1,2-a][1,2,5]triazepine-1(S)—carboxylic acid (diastereoisomer 1).

The compounds of formula I and their aforementioned pharmaceutically acceptable salts can be used as medicaments in the form of pharmaceutical preparations which contain them in association with a compatible pharmaceutical carrier material. This carrier material can be an organic or inorganic carrier material which is suitable for enteral, for example, oral, or parenteral administration, examples of such carrier materials are water, gelatin, gum arabic, lactose, starch, magnesium stearate, talc, vegetable oils, polyalkylene glycols, petroleum jelly and the like. The pharmaceutical preparations can be made up in a solid form, for example, as tablets, dragees, suppositories or capsules, or in a liquid form, for example, as solutions, suspensions or emulsions. The pharmaceutical preparations may be subjected to standard pharmaceutical operations, such as, sterilization and/or may contain adjuvants, such as, preserving, stabilizing, wetting or emulsifying agents, salts for varying the osmotic pressure or buffers. The pharmaceutical preparations may also contain other therapeutically valuable substances.

The compounds of formula I and their aforementioned pharmaceutically acceptable salts can be administered to adults in a daily dosage of from about 0.1 mg to 100 mg, preferably about 1 mg to 50 mg, per kilogram body weight. The daily dosage may be administered as a single dose or in divided doses. It will be appreciated that the aforementioned dosage range is given by way of example only and can be varied upwards or downwards depending on factors, such as, the particular compound or salt being administered, the route of administration, the severity of the indication being treated and the condition of the host, that is, warm-blooded animal, as determined by the person administering the treatment.

The Examples which follow further illustrate the invention. The temperatures given are in degrees Centigrade unless otherwise stated.

EXAMPLE 1

2.0 g of tert.butyl octahydro-9-methylene-6,10-dioxo-6H-pyridazo [1,2-a][1,2]diazepine-1(S)-carboxylate and 1.0 ml of thiolacetic acid in 20 ml of dichloromethane were stirred at room temperature for 20 hours. After evaporation the residual oil was chromatographed on silica gel using ethyl acetate/n-hexane for the elution, whereby there were obtained firstly 1.3 g (52%) of tert.butyl 9(S)-acetylthiomethyl-octahydro-6,10-dioxo-6H-pyridazo[1,2-a][1,2]diazepine-1(S)-carboxylate as a white solid of melting point 95°–96° C. (from diethyl ether/n-hexane), and subsequently 1.16 g (46%) of tert.butyl 9(R)-acetylthiomethyl-octahydro-6,10-dioxo-6H-pyridazo[1,2-a][1,2]diazepine-1(S)-carboxylate as an amorphous white solid.

The tert.butyl octahydro-9-methylene-6,10-dioxo-6H-pyridazo[1,2-a][1,2]diazepine-1(S)-carboxylate used as the starting material was prepared as follows:

A solution of 10 g of 1-benzyloxycarbonyl-S-piperazic acid tert.butyl ester in 100 ml of methanol was hydrogenated at room temperature and atmospheric pressure over 5% palladium/carbon. The catalyst was removed by filtration and the filtrate was evaporated to dryness. The resulting crude piperazic acid tert.butyl ester was taken up in 100 ml of dioxane, and the solution was cooled to 0° C. and treated with a solution of 3.94 g of a-methylene-glutaric anhydride in 100 ml of dioxane. The mixture was stirred at 20° C. for 18 hours and the solvent was removed by evaporation. The residue was partitioned between methyl tert.butyl ether and saturated sodium bicarbonate solution. The aqueous phase was acidified with hydrochloric acid and extracted with dichloromethane to give 8.34 g (85%) of 3(S)-tert.-butoxycarbonyl-hexahydro-α-methylene-δ-oxo-1-pyrida-zinepentanoic acid in the form of white crystals of melting point 96°-99° C. A 5.0 g position of this acid was taken up in 350 ml of tetrahydrofuran and the solution was cooled to 0° C. Thereafter, 3.75 g of phosphorus pentachloride were added and the mixture was stirred at 0° C. for 1 hour and at 20° C. for 18 hours. The solvent was removed by evaporation and the residue was partitioned between ethyl acetate and saturated sodium bicarbonate solution. The organic phase was evaporated and the residue was chromatographed on silica gel using ethyl acetate/n-hexane for the elution, whereby there were obtained 3.7 g (79%) of tert.-butyl octahydro-9-methylene-6,10-dioxo-6H-pyridazo[1,2-a]-[1,2]diazepine-1(S)-carboxylate as a white solid of melting point 105°-106° C. (from hexane).

EXAMPLE 2

370 mg of tert.butyl 9(S)-acetylthiomethyloctahydro-6,10-dioxo-6H-pyridazo[1,2-a][1,2]diazepine-1(S)-carboxylate were dissolved in 5 ml of tetrahydrofuran and the solution was treated at 0° C. with 2 ml of 0.5M borane/tetrahydrofuran. The mixture was stirred at 0° C. for 1 hour and at 20° C. for an additional 3 hours, and then diluted with dichloromethane. 15 ml of dilute hydrochloric acid were added carefully and the mixture was stirred at 0° C. for 0.5 hour. The mixture was adjusted to pH 8 with sodium carbonate and the phases were separated. The organic phase was evaporated and the residue was chromatographed on silica gel using ethyl acetate/n-hexane for the elution, whereby there were obtained 150 mg (42%) of tert.butyl 9(S)-acetylthiomethyl-octahydro-10-oxo-6H-pyridazo[1,2-a][1,2]diazepine-1(S)-carboxylate as a colorless oil.

EXAMPLE 3

In a manner analogous to that described in Example 2, from 370 mg of tert.butyl 9(R)-acetylthiomethyloctahydro-6,10-dioxo-6H-pyridazo[1,2-a][1,2]diazepine-1(S)-carboxylate there were obtained 200 mg (56%) of tert.butyl 9(R)-acetylthiomethyl-octahydro-10-oxo-6H-pyridazo[1,2-a][1,2]diazepine-1(S)-carboxylate as a colorless oil.

EXAMPLE 4

300 mg of tert.butyl 9(S)-acetylthiomethyl-octahydro-6,10-dioxo-6H-pyridazo[1,2-a][1,2]-diazepine-1(S)-carboxylate were dissolved in 3 ml of trifluoroacetic acid and the solution was left to stand at 20° C. for 1.5 hours. After evaporation, there were obtained 230 mg (90%) of 9(S)-acetylthiomethyl-octahydro-6,10-dioxo-6H-pyridazo-[1,2-a][1,2]pyridazine-1(S)-carboxylic acid as a white solid of melting point 133°-135° C. (from ethyl acetate/n-hexane).

EXAMPLE 5

In a manner analogous to that described in Example 4, from 300 mg of tert.butyl 9(R)-acetylthio-methyloctahydro-6,10-dioxo-6H-pyridazo[1,2-a][1,2]-diazepine-1(S)-carboxylate, there were obtained 235 mg of 9(R)-acetylthiomethyl-octahydro-6,10-dioxo-6H-pyridazo[1,2-a][1,2]diazepine-1(S)-carboxylic acid as an amorphous white solid.

EXAMPLE 6

In a manner analogous to that described in Example 4, from 130 mg of tert.butyl 9(S)-acetylthiomethyl-octahydro-10-oxo-6H-pyridazo [1,2-a][1,2]diazepine-1(S)-carboxylate, there were obtained 105 mg of (S)-acetylthiomethyl-octahydro-10-oxo-6H-pyridazo[1,2-a][1,2]diazepine-1(S)-carboxylic acid as a white foam.

EXAMPLE 7

In a manner analogous to that described in Example 4, from 180 mg of tert.butyl 9(R)-acetylthiomethyl-octahydro-10-oxo-6H-pyridazo[1,2-a][1,2]diazepine-1(S)-carboxylate, there were obtained 150 mg of 9(R)-acetylthiomethyl-octahydro-10-oxo-6H-pyridazo[1,2-a][1,2]diazepine-1(S)-carboxylic acid as a colorless gum.

EXAMPLE 8

160 mg of 9(S)-acetylthiomethyl-octahydro-6,10-dioxo-6H-pyridazo[1,2-a][1,2diazepine-1(S)-carboxylic acid were dissolved in 1.6 ml of water containing 1.6 ml of concentrated ammonium hydroxide and the mixture was left to stand at 20° C. for 1 hour. The mixture was then adjusted to pH 1 with hydrochloric acid and extracted with dichloromethane. The dichloromethane extract was evaporated and the residue was triturated with n-hexane, whereby there were obtained 116 mg of octahydro-9(S)-mercaptomethyl-6,10-dioxo-6H-pyridazo[1,2-a][1,2]diazepine-1(S)-carboxylic acid as an amorphous solid.

EXAMPLE 9

In a manner analogous to that described in Example 8, from 210 mg of 9(R)-acetylthiomethyl-octahydro-6,10-dioxo-6H-pyridazo[1,2-a][1,2]diazepine-1(S)-carboxylic acid, there were obtained 75 mg of octahydro-9(R)-mercaptomethyl-6,10-dioxo-6H-pyridazo[1,2-a][1,2]diazepine-1(S)-carboxylic acid as an amorphous solid.

EXAMPLE 10

In a manner analogous to that described in Example 8, from 110 mg of 9(S)-acetylthiomethyl-octahydro-10-oxo-6H-pyridazo[1,2-a][1,2]diazepine-1(S)-carboxylic acid, there were obtained 75 mg of octahydro-9(S)-mercaptomethyl-10-oxo-pyridazo[1,2-a][1,2]diazepine-1(S)-carboxylic acid as an amorphous solid.

EXAMPLE 11

In a manner analogous to that described in Example 8, from 165 mg of 9(R)-acetylthiomethyl-octahydro-10-oxo-6H-pyridazo[1,2-a][1,2]diazepine-1(S)-carboxylic acid, there were obtained 100 mg of octahydro-9(R)-mercaptomethyl-10-oxo-6H-pyridazo [1,2-a][1,2]diazepine-1(S)-carboxylic acid as an amorphous solid.

EXAMPLE 12

In a manner analogous to that described in Example 1, from 0.36 g of tert.butyl decahydro-10-methylene-6,11-dioxo-6H-pyridazo[1,2-a][1,2]diazocine-1(S)-carboxylate, there was obtained 0.21 g of tert.butyl 10(R,S)-acetylthiomethyl-decahydro-6,11-dioxo-6H-pyridazo[1,2-a][1,2]-diazocine-1(S)-carboxylate in the form of a white solid of melting point 105°–108°, from methyl tert.butyl ether.

The tert.butyl decahydro-10-methylene-6,11-dioxo-6H-pyridazo[1,2-a][1,2]diazocine-1(S)-carboxylate used as the starting material was prepared as follows:

A solution of 1.86 g of 1-ethyl hydrogen 2-methylenehexanedioate in 25 ml of anhydrous tetrahydrofuran was cooled to −10° C. and stirred during the addition of 1.01 g of triethylamine and 1.37 g of isobutyl chloroformate. The mixture was stirred at −10° C. for 15 minutes and a solution of 1.86 g of piperazic acid tert.butyl ester in 25 ml of anhydrous tetrahydrofuran was then added. The mixture was stirred at −10° C. for 30 minutes and then at room temperature for 16 hours. The solvent was removed by evaporation and the residue was partitioned between ethyl acetate and 1N aqueous hydrochloric acid. The organic phase was washed with saturated sodium chloride solution and saturated aqueous sodium bicarbonate solution and then evaporated to give 1.99 g of tert.butyl 1-[5-(ethoxycarbonyl)-5-hexenoly]-hexahydro-3(S)-pyridazinecarboxylate in the form of a white solid of melting point 63°–65° C., from ethyl acetate/n-hexane.

A solution of 8.2 g of tert.butyl 1-[5-(ethoxycarbonyl)-5-hexenoyl]-hexahydro-3-(S)-pyridazinecarboxylate in 25 ml of ethanol was treated with 23.7 ml of 1N aqueous sodium hydroxide solution for 16 hours. The solution was diluted with 80 ml of water and the volume was then reduced to 80 ml by evaporation. The solution was washed with diethyl ether and the pH of the aqueous solution was adjusted to 3 using 2N aqueous hydrochloric acid. The solution was then extracted with dichloromethane. The organic solution was evaporated and the residue was chromatographed on silica gel using dichloromethane/methanol (9:1) for the elution, whereby there were obtained 3.62 g of tert.butyl 1-[5-(carboxy)-5-hexenoyl]-hexahydro-3(S)-pyridazinecarboxylate in the form of a white solid of melting point 86°–88° C., from n-hexane.

A solution of 0.56 g of tert.butyl 1-[5-(carboxy)-5-hexenoyl]-hexahydro-3(S)-pyridazinecarboxylate in 12 ml of dichloromethane was treated with 0.31 g of thionyl chloride and the solution obtained was stirred at room temperature under a slow stream of nitrogen for 20 hours. The solution was washed with saturated aqueous sodium bicarbonate solution and evaporated. The residue was chromatographed on silica gel using diethyl ether for the elution, whereby there was obtained 0.21 g of tert.butyl decahydro-10-methylene-6,11-dioxo-6H-pyridazo[1,2-a]-[1,2]-diazocine-1(S)-carboxylate in the form of a white solid of melting point 108°–110° C., from diethyl ether.

EXAMPLE 13

0.19 g of tert.butyl 10(R,S)-acetylthiomethyl-decahydro-6,11-dioxo-6H-pyridazo [1,2-a][1,2]diazocine-1(S)-carboxylate was treated with 2 ml of trifluoroacetic acid at room temperature for 2 hours. The mixture was evaporated. The residue was taken up in toluene and evaporated. This procedure was repeated twice. The residue was stirred under nitrogen with 1.5 ml of concentrated aqueous ammonia and 1.5 ml of water at room temperature for 1.5 hours. The solution was cooled to 0° C. and the pH was adjusted to 1 using concentrated hydrochloric acid. The solution was then saturated with sodium chloride and extracted with dichloromethane. The organic solution was evaporated to give 75 mg of decahydro-10(R,S)-mercaptomethyl-6,11-dioxo-6H-pyridazo[1,2-a][1,2]diazocine-1(S)-carboxylic acid in the form of an amorphous white solid.

EXAMPLE 14

720 mg of tert.butyl 8-benzyl-octahydro-9-methanesulfonyloxymethyl-6,10-dioxo-6H-pyridazo[1,2-a][1,2,5]triazepine-1(S)-carboxylate, diastereoisomer 1, were dissolved in 20 ml of butan-2-one and the solution was treated with 340 mg of potassium thiolacetate. The mixture was heated under reflux for 8 hours and then evaporated to dryness. The residue was partitioned between ethyl acetate and water. The organic phase was washed successively with aqueous sodium bicarbonate solution and saturated sodium chloride solution, dried over anhydrous sodium sulfate and evaporated. The residue was chromatographed on silica gel using ethyl acetate/n-hexane for the elution, whereby there were obtained 400 mg of tert.butyl 9-acetylthiomethyl-8-benzyl-octahydro-6,10-dioxo-6H-pyridazo[1,2-a][1,2,5]triazepine-1(S)-carboxylate, diastereoisomer 1, in the form of yellow crystals of melting point 156°–158° C., from ethyl acetate/n-hexane.

The tert.butyl 8-benzyl-octahydro-9-methanesulfonyloxymethyl-6,10-dioxo-6H-pyridazo[1,2-a][1,2,5]triazepine-1(S)-carboxylate, diastereoisomer 1, used as the starting material was prepared as follows:

A solution of 20 g of 1-benzyloxy-carbonyl-S-piperazic acid tert.butyl ester in 400 ml of ethanol was hydrogenated for 5 hours at atmospheric pressure over 2 g of 5% palladium/carbon. The catalyst was removed by filtration and the filtrate was evaporated. The residue was stirred with a mixture of 50 ml of dichloromethane and 75 ml of aqueous sodium bicarbonate solution at 0° C., during the addition over a period of 15 minutes of 5.16 ml of bromoacetyl chloride dissolved in 150 ml of dichloromethane. The mixture was stirred for an additional 45 minutes and then the layers were separated. The organic layer was dried over anhydrous sodium sulfate and evaporated. The residue was chromatographed on silica gel using ethyl acetate/n-hexane for the elution, whereby there were obtained 9.9 g of tert.butyl 1-bromoacetyl-hexahydro-3(S)-pyridazinecarboxylate in the form of a white solid of melting point 99°–101° C., from ethyl acetate/n-hexane.

13.9 g of N-trifluoroacetyl-O-benzyl-D,L-serine were dissolved in 150 ml of dichloromethane and the solution was cooled to −20° C. The solution was treated at this temperature with 9.96 g of phosphorus pentachloride, allowed to come to room temperature and then stirred at room temperature for 30 minutes. After evaporation, there was obtained an oily residue which was dissolved in 150 ml of dichloromethane. The solution was added within 1 hour at 0° C. to a stirred mixture of 9.8 g of tert.butyl 1-bromoacetyl-hexahydro-3(S)-pyridazinecarboxylate, 100 ml of dichloromethane and 100 ml of aqueous sodium bicarbonate solution. The mixture was stirred at room temperature for 17 hours and the layers were separated. The organic layer was dried over anhydrous sodium sulfate and evaporated. The residue was chromatographed on silica gel using ethyl acetate/n- hexane for the elution, whereby there were obtained 12.5 g of tert.butyl 1-bromoacetyl-2-/[3-benzyloxy-2(R,S)-trifluoroacetylamino]propanoyl/pyridazine-3(S)-carboxylate in the form of a yellow oil.

The above oil was dissolved in 650 ml of dry dimethylformamide and the solution was treated with 980 mg of sodium hydride. After 2 hours at 20° C., the solution was poured on to 1.6 l of ice-water and extracted with dichloromethane. The organic extract was evaporated and the residue was chromatographed on silica gel using ethyl acetate/n-hexane for the elution, whereby there were obtained two diastereoisomers, 3.1 g of diastereoisomer 1 and 1.05 g of diastereoisomer 2, respectively, of tert.butyl 9-benzyloxymethyl-octahydro-6,10-dioxo-6H-pyridazo-[1,2-a][1,2,5]triazepine-1(S)-carboxylate in the form of pale yellow gums.

500 mg of diasteroisomer 1 above were dissolved in 10 ml of methanol containing a few drops of acetic acid and the solution was hydrogenated at atmospheric pressure over 50 mg of 5% palladium/carbon for 17 hours. The catalyst was removed by filtration and the filtrate was evaporated to give 440 mg of tert.butyl octahydro-9-hydroxymethyl-6,10-dioxo-6H-pyridazo[1,2-a][1,2,5]triazepine-1(S)-carboxylate, diastereoisomer 1, in the form of a colorless gum.

The above gum was reacted with 0.41 ml of benzyl bromide in 20 ml of acetonitrile containing 1 ml of diethylisopropylamine at 20° C. for 24 hours. After evaporation and chromatography of the residue on silica gel using ethyl acetate/n-hexane for the elution, there were obtained 400 mg of tert.butyl 8-benzyl-octahydro-9-hydroxymethyl-6,10-dioxo-6H-pyridazo[1,2-a][1,2,5]triazepine-1(S)-carboxylate, diastereoisomer 1, in the form of a white solid of melting point 133°–135° C., from ethyl acetate/n-hexane.

265 mg of tert.butyl 8-benzyl-octahydro-9-hydroxymethyl-6,10-dioxo-6H-pyridazo[1,2-a][1,2,5]triazepine-1(S)-carboxylate, diastereoisomer 1, in 10 ml of dichloromethane were treated at 20° C. with 0.2 ml of triethylamine and then with 0.09 ml of methanesulfonyl chloride. The mixture was stirred at room temperature for 2 hours, washed with water, dried over anhydrous sodium sulfate and evaporated to give 230 mg of tert.butyl 8-benzyl-octahydro-9-methanesulfonyloxymethyl-6,10-dioxo-6H-pyridazo[1,2-a][1,2,5]triazepine-1(S)-carboxylate, diastereoisomer 1, in the form of a white solid of melting point 55°–57° C., from diethyl ether/n-hexane.

EXAMPLE 15

110 mg of tert.butyl 9-acetylthiomethyl-8-benzyl-octahydro-6,10-dioxo-6H-pyridazo[1,2-a][1,2,5]triazepine-1(S)-carboxylate, diastereoisomer 1, were treated with 0.5 ml of 45% hydrogen bromide in acetic acid at 20° C. for 30 minutes. Anhydrous diethyl ether was then added and the precipitated product was filtered, whereby 60 mg of amorphous 9-acetylthiomethyl-8-benzyl-octahydro-6,10-dioxo-6H-pyridazo[1,2-a][1,2,5]triazepine-1(S)-carboxylic acid hydrobromide, diastereoisomer 1, were obtained.

EXAMPLE 16

In a manner analogous to that described in Example 8, from 60 mg of 9-acetylthiomethyl-8-benzyl-octahydro-6,10-pyridazo[1,2-a][1,2,5]triazepine hydrobromide, there were obtained, after chromatography on silica gel using 2% acetic acid in diethyl ether for the elution, 20 mg of 8-benzyl-octahydro-9-mercaptomethyl-6,10-dioxo-6H-pyridazo[1,2-a][1,2,5]triazepine-1(S)-carboxylic acid, diastereoisomer 1, in the form of a white solid of melting point 85° C. decomposition; from diethyl ether/n-hexane.

EXAMPLE 17

In a manner analogous to that described in Example 14, from tert.butyl 8-methyl-octahydro-9-methanesulfonyloxymethyl-6,10-dioxo-6H-pyridazo[1,2-a][1,2,5]triazepine-1(S)-carboxylate, there were obtained two diastereoisomers, diastereoisomer 1 and diastereoisomer 2, of tert.butyl 9-acetylthiomethyl-8-methyl-octahydro-6,10-dioxo-6H-pyridazo[1,2-a][1,2,5]triazepine-1(S)-carboxylate in the form of gums.

The tert.butyl 8-methyl-octahydro-9-methanesulfonyloxymethyl-6,10-dioxo-6H-pyridazo[1,2-a][1,2,5]triazepine-1(S)-carboxylate used as the starting material was obtained in the form of a gum in a manner analogous to that described in Example 14 for the preparation of the starting material used therein.

EXAMPLE 18

In a manner analogous to that described in Example 15, from 110 mg of tert.butyl 9-acetylthiomethyl-8-methyloctahydro-6,10-dioxo-6H-pyridazo[1,2-a][1,2,5]triazepine-1(S)-carboxylate, diastereoisomer 1, there were obtained 100 mg of 9-acetylthiomethyl-8-methyl-octahydro-6,10-dioxo-6H-pyridazo [1,2-a][1,2,5]triazepine-1(S)-carboxylic acid, diastereoisomer 1, in the form of an amorphous solid.

EXAMPLE 19

In a manner analogous to that described in Example 15, from 80 mg of tert.butyl 9-acetylthiomethyl-8-methyl-octahydro-6,10-dioxo-6H-pyridazo [1,2-a][1,2,5]triazepine-1(S)-carboxylate, diastereoisomer 2, there were obtained 50 mg of 9-acetylthiomethyl-8-methyl-octahydro-6,10-dioxo-6H-pyridazo[1,2-a][1,2,5]triazepine-1(S)-carboxylic acid, diastereoisomer 2, in the form of an amorphous solid.

EXAMPLE 20

In a manner analogous to that described in Example 8, from 50 mg of 9-acetylthiomethyl-8-methyl-octahydro-6,10-dioxo-6H-pyridazo[1,2-a][1,2,5]triazepine-1(S)-carboxylic acid, diastereoisomer 1, there were obtained 10 mg of octahydro-9-mercaptomethyl-8-methyl-6,10-dioxo-6H-pyridazo[1,2-a][1,2,5]triazepine-1(S)-carboxylic acid, diastereoisomer 1, in the form of a white lyophilizate.

EXAMPLE 21

In a manner analogous to that described in Example 8, from 50 mg of 9-acetylthiomethyl-8-methyl-octahydro-6,10-dioxo-6H-pyridazo[1,2-a][1,2,5]triazepine-1(S)-carboxylic acid, diastereoisomer 2, there were obtained 10 mg of octahydro-9-mercaptomethyl-8-methyl-6,10-dioxo-6H-pyridazo[1,2-a][1,2,5]triazepine-1(S)-carboxylic acid, diastereoisomer 2, in the form of a white lyophilizate.

EXAMPLE 22

In a manner analogous to that described in Example 1, from 2.02 g of methyl octahydro-9-methylene-6,10-dioxo-6H-pyridazo[1,2-a][1,2]diazepine-1(S)-carboxylate, there were obtained 1.17 g of methyl 9(S)-acetylthiomethyloctahydro-6,10-dioxo-6H-pyridazo[1,2-a][1,2]diazepine-1(S)-carboxylate in the form of white crystals of melting point 127°-129° C., from diethyl ether/n-hexane, and 1.2 g of methyl 9(R)-acetylthiomethyl-octahydro-6,10-dioxo-6H-pyridazo[1,2-a][1,2]diazepine-1(S)-carboxylate in the form of a colorless gum.

The methyl octahydro-9-methylene-6,10-dioxo-6H-pyridazo[1,2-a][1,2]diazepine-1(S)-carboxylate used as the starting material was prepared as follows:

10 g of tert.butyl octahydro-9-methylene-6,10-dioxo-6H-pyridazo[1,2-a][1,2]diazepine-1(S)-carboxylate, prepared as described in Example 1, were stirred with 40 ml of trifluoroacetic acid at 20° C. for 3 hours. The mixture was evaporated and the oil obtained was treated with diethyl ether to give 7.6 g of octahydro-9-methylene-6,10-dioxo-6H-pyridazo [1,2-a][1,2]diazepine-1(S)-carboxylic acid in the form of a white solid of melting point 169°-172° C.

7.6 g of octahydro-9-methylene-6,10-dioxo-6H-pyridazo[1,2-a][1,2]diazepine-1(S)-carboxylic acid were suspended in 200 ml of ethyl acetate and the suspension was stirred at 0° C. during the addition of 100 ml of ethereal diazomethane solution. After 30 minutes, excess diazomethane was destroyed by the dropwise addition of acetic acid. The mixture was washed with aqueous sodium bicarbonate solution, dried over sodium sulfate and evaporated to give 5.17 g of methyl octahydro-9-methylene-6,10-dioxo-6H-pyridazo[1,2-a][1,2]diazepine-1(S)-carboxylate in the form of a white solid of melting point 73°-75° C., from n-hexane.

The Examples which follow illustrate pharmaceutical preparations containing the compounds of formula I of the invention:

EXAMPLE A

Tablets containing the following ingredients can be produced in a conventional manner:

| Ingredient | Per tablet |
| --- | --- |
| A compound of formula I | 10.0 mg |
| Lactose | 125.0 mg |
| Maize starch | 75.0 mg |
| Talc | 4.0 mg |
| Magnesium stearate | 1.0 mg |
| Total weight | 215.0 mg |

EXAMPLE B

Capsules containing the following ingredients can be produced in a conventional manner:

| Ingredient | Per capsule |
| --- | --- |
| A compound of formula I | 25.0 mg |
| Lactose | 150.0 mg |
| Maize starch | 20.0 mg |
| Talc | 5.0 mg |
| Total capsule content | 200.0 mg |

We claim:
1. A compound of the formula

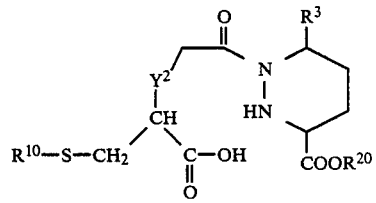

VI wherein $R^3$ is hydrogen or phenyl or phenyl substituted with one or more substiuents selected from halogen, alkyl having 1 to 4 carbon atoms, alkoxy having 1 to 6 carbon atoms and trifluromethyl; $R^{10}$ is alkanoyl having up to 8 carbon atoms or benzoyl or benzoyl substituted with one or more substiuents selected from halogen, alkyl having 1 to 4 carbon atoms, alkoxy having 1 to 6 carbon atoms and trifluoromethyl, $R^{20}$ is alkyl having 1 to 4 carbon atoms; and $Y^2$ is —$CH_2$— or —$CH_2CH_2$—.

* * * * *

UNITED STATES PATENT AND TRADEMARK OFFICE
CERTIFICATE OF CORRECTION

PATENT NO. : 4,826,980

DATED : May 2, 1989

INVENTOR(S) : Cedric Herbert Hassall, et al

It is certified that error appears in the above-identified patent and that said Letters Patent is hereby corrected as shown below:

On the title under Related U.S. Application Data

"Division of Ser. No. 48,172, May 11, 1987, Pat. No. 4,785,893, which is a division of Ser. No. 767,372, Aug. 12, 1985, Pat. No. 4,692,438, should read --Division of Ser. No. 48,172, May 11, 1987, Pat. No. 4,785,093, which is a division of Ser. No. 764,372, August 12, 1985, Pat. No. 4,692,438--.

Signed and Sealed this

Twenty-seventh Day of March, 1990

Attest:

JEFFREY M. SAMUELS

*Attesting Officer*  *Acting Commissioner of Patents and Trademarks*